United States Patent
Tanaka et al.

(10) Patent No.: US 9,241,880 B2
(45) Date of Patent: Jan. 26, 2016

(54) DENTAL GLASS IONOMER CEMENT COMPOSITION

(75) Inventors: Koji Tanaka, Itabashi-ku (JP); Daisuke Ota, Itabashi-ku (JP); Hideki Yarimizu, Itabashi-ku (JP)

(73) Assignee: GC CORPORATION, Tokyo (JP)

( * ) Notice: Subject to any disclaimer, the term of this patent is extended or adjusted under 35 U.S.C. 154(b) by 664 days.

(21) Appl. No.: 13/242,917

(22) Filed: Sep. 23, 2011

(65) Prior Publication Data
US 2012/0077901 A1 Mar. 29, 2012

(30) Foreign Application Priority Data
Sep. 28, 2010 (JP) ................................ 2010-216576

(51) Int. Cl.
*A61K 6/08* (2006.01)
*A61K 6/083* (2006.01)
*A61K 6/00* (2006.01)

(52) U.S. Cl.
CPC ............. *A61K 6/0835* (2013.01); *A61K 6/0047* (2013.01); *A61K 6/0091* (2013.01)

(58) Field of Classification Search
CPC ... A61K 6/005; A61K 6/0091; A61K 6/0097; A61K 6/08; A61K 6/0835
USPC ....................................................... 523/116
See application file for complete search history.

(56) References Cited

U.S. PATENT DOCUMENTS

| | | |
|---|---|---|
| 5,064,495 A | 11/1991 | Omura et al. |
| 5,085,726 A | 2/1992 | Omura et al. |
| 5,670,657 A | 9/1997 | Kojima et al. |
| 2003/0055123 A1 | 3/2003 | Kawashima et al. |
| 2003/0136303 A1 | 7/2003 | Kobayashi et al. |
| 2007/0043141 A1* | 2/2007 | Wu et al. ........................ 523/115 |

FOREIGN PATENT DOCUMENTS

| | | |
|---|---|---|
| EP | 0 277 413 A2 | 8/1988 |
| EP | 0 277 413 A3 | 8/1988 |
| EP | 1 269 968 A1 | 1/2003 |
| EP | 1 319 386 A1 | 6/2003 |
| JP | 2002-265312 | 9/2002 |
| JP | 2003-12433 | 1/2003 |
| JP | 2008-56649 | 3/2008 |
| JP | 2009-67746 | 4/2009 |

OTHER PUBLICATIONS

Extended Search Report issued Nov. 22, 2011 in European Patent Application No. 11007845.8-1521.

* cited by examiner

*Primary Examiner* — Michael Pepitone
(74) *Attorney, Agent, or Firm* — Oblon, McClelland, Maier & Neustadt, L.L.P.

(57) ABSTRACT

To provide a dental glass ionomer cement composition having excellent adhesion strength to a metallic prosthesis. A dental glass ionomer cement composition includes a copolymer (A), a fluoroaluminosilicate glass powder (B) and water (C). The copolymer (A) includes a polymer or copolymer of α-β unsaturated carboxylic acid, or includes a copolymer of α-β unsaturated carboxylic acid and one or more kinds selected from a group of acrylamide, acrylonitrile, methacrylic acid ester, acrylates, vinyl chloride, allyl chloride and vinyl acetate. In the copolymer (A), the number of molecules of α-β unsaturated carboxylic acid occupies 50% or more of the total number of molecules. The dental glass ionomer cement composition further includes a compound (D) which contains a sulfur atom in one molecule, includes a carboxylic group and an amino group and does not include a polymerizable group.

8 Claims, No Drawings

DENTAL GLASS IONOMER CEMENT COMPOSITION

BACKGROUND OF THE INVENTION

1. Field of the Invention

The present invention relates to a dental glass ionomer cement composition having excellent adhesion strength to a metallic prosthesis.

2. Description of the Conventional Art

In dental treatments, cement materials such as zinc phosphate cement, glass ionomer cement, resin cement and the like have been used as a material for bonding a dental prosthesis such as a crown, an inlay, a bridge or the like to a tooth lost part damaged due to a dental caries, an accident or the like. In the basic concept for restoring a tooth lost part, a material having a suitable strength is used in a space between the tooth lost part and the prosthesis so as to bond them.

Among these materials for bonding the prosthesis, dental glass ionomer cement mainly including polycarboxylic acid, a fluoroaluminosilicate glass powder and water is cured by acid-base reaction of polycarboxylic acid and fluoroaluminosilicate glass powders under the existence of water. It has been known that the dental glass ionomer cement releases fluoride effective for strengthening a tooth. In addition, the dental glass ionomer cement has been widely used as an excellent dental material having high hydrophilicity and excellent adhesiveness to the tooth. However, since the dental glass ionomer cement has low chemical interaction of polycarboxylic acid to the metallic prosthesis, it has been difficult to acquire sufficient adhesiveness.

A resin-reinforced glass ionomer cement acquired by adding a (meth)acrylate monomer to the dental glass ionomer cement as a resin component has been used. The resin-reinforced glass ionomer cement can increase a bending strength of a cured body by visco-tenacity of the polymerized resin component, so that frictional force increases between the cement and the prosthesis. Thus, mechanical retentivity between the tooth and the prosthesis is improved. However, since the resin component hardly has interaction with the metallic prosthesis, there is no effect to improve chemical adhesion strength.

Accordingly, in order to acquire adhesiveness to the tooth, adhesive resin-reinforced glass ionomer cement blended with a polymerizable monomer having an acid group has been discussed (e.g., refer to Japanese Patent Application Laid-Open No. 2003-012433). The patent application No. 2003-012433 discusses that, in the polymerizable monomer having an acid group, a polymerizable monomer having a thiophosphoric acid group is preferably used because of having excellent adhesiveness to the prosthesis. Since the polymerizable monomer having a thiophosphoric acid group includes, in its structure, a sulfur atom with high compatibility to metal, the adhesiveness to the metallic prosthesis is improved. However, polymerizability is lower than the other polymerizable monomers, and there is a problem that the adhesion strength may decrease when polymerization is insufficient. When the amount of a polymerization initiator increases so as to secure the polymerizability, there is a problem that stability of a product decreases.

Furthermore, when the metallic prosthesis is bonded using the resin cement, various kinds of surface treatment agents (primers) are used to increase the adhesiveness. Specifically, in a treatment of a metallic prosthesis mainly including gold, platinum, palladium, silver and the like, surface treatment agents including a polymerizable monomer having a functional group containing a sulfur atom (a primer for metal) have been used (e.g., refer to Japanese Patent Application Laid-Open Nos. 2002-265312, 2008-056649 and 2009-067746). These surface treatment agents have high compatibility to metal, which is induced by a sulfur atom contained in a specific functional group in the surface agents. In addition, a polymerization group in the surface treatment agent is copolymerized with a matrix of the resin cement. Accordingly, the surface treatment agents can exercise effect to increase the adhesiveness of a resin component with metal. However, comparing with the resin cement which needs a surface treatment, the dental glass ionomer cement has an advantage which can bond to the tooth without performing the surface treatment. Thus, when the dental glass ionomer cement is used, it is not desirable with the latest tendency to take much time and effort to use the metallic primer on the surface of the metallic prosthesis.

SUMMARY OF THE INVENTION

An objective of the present invention is to provide a dental glass ionomer cement composition having an excellent adhesion strength to a metallic prosthesis.

Means for Solving the Problem

Present inventors carried out earnest works to solve the aforementioned problems and, as a result, they found out the following composition to complete the present invention. A dental glass ionomer cement composition includes a copolymer (A), a fluoroaluminosilicate glass powder (B), and water (C). The copolymer (A) includes a polymer or copolymer of $\alpha$-$\beta$ unsaturated carboxylic acid, or includes a copolymer of $\alpha$-$\beta$ unsaturated carboxylic acid and one or more kinds selected from a group of acrylamide, acrylonitrile, methacrylic acid ester, acrylates, vinyl chloride, allyl chloride and vinyl acetate. In the copolymer (A), the number of molecules of $\alpha$-$\beta$ unsaturated carboxylic acid occupies 50% or more of the total number of molecules. The dental glass ionomer cement composition is blended with a compound (D) which contains a sulfur atom in one molecule, includes a carboxylic group and an amino group, and does not include a polymerizable group. With this composition, a functional group containing the sulfur atom in the compound (D) indicates compatibility with metal. Further, the carboxylic group and amino group in the compound (D) interact with the copolymer (A) by hydrogen bond, where the copolymer (A) mainly includes the polymer or copolymer of $\alpha$-$\beta$ unsaturated carboxylic acid as a matrix component of glass ionomer cement, or includes $\alpha$-$\beta$ unsaturated carboxylic acid. In addition, the carboxylic group and amino group in the compound (D) interact with a metallic element existing in the fluoroaluminosilicate glass powder (B). Therefore, high adhesion strength can be obtained. Furthermore, since the compound (D) does not include a polymerization group in its structure, decreasing of adhesion strength caused by an easiness of polymerization does not occur.

More specifically, according to an aspect of the present invention, a dental glass ionomer cement composition includes a copolymer (A), a fluoroaluminosilicate glass powder, (B) and water (C). The copolymer (A) includes a polymer or copolymer of $\alpha$-$\beta$ unsaturated carboxylic acid, or includes a copolymer of $\alpha$-$\beta$ unsaturated carboxylic acid and one or more kinds selected from a group of acrylamide, acrylonitrile, methacrylic acid ester, acrylates, vinyl chloride, allyl chloride and vinyl acetate. In the copolymer (A), the number of molecules of $\alpha$-$\beta$ unsaturated carboxylic acid occupies 50% or more of the total number of molecules. The dental glass ionomer cement composition further includes a compound (D) which contains a sulfur atom in one molecule, includes a carboxylic group and an amino group and does not include a polymerizable group.

Further, the compound (D) containing a sulfur atom in one molecule, including a carboxylic group and an amino group and not including a polymerizable group can have a structure in which the sulfur atom is not adjacent to an oxygen atom in the molecule. Further, the compound (D) containing a sulfur atom in one molecule, including a carboxylic group and an amino group and not including a polymerizable group can have the content of 0.01 to 10% by weight. Furthermore, the compound (D) containing a sulfur atom in one molecule, including a carboxylic group and an amino group and not including a polymerizable group can have a structure in which the sulfur atom has, in the molecule, a thiol (—SH) structure, a sulfide (—S—) structure or a disulfide (—S—S—) structure. In these compounds, the functional group containing the sulfur atom in the compound (D) indicates stronger compatibility to metal, so that it is preferable.

Further, the dental glass ionomer cement composition according to the present invention can be configured with a first component and a second component. The first component includes the copolymer (A) and water (C). The copolymer (A) includes a polymer or copolymer of α-β unsaturated carboxylic acid, or includes a copolymer of α-β unsaturated carboxylic acid and one or more kinds selected from a group of acrylamide, acrylonitrile, methacrylic acid ester, acrylates, vinyl chloride, allyl chloride and vinyl acetate. In the copolymer (A), the number of molecules of α-β unsaturated carboxylic acid occupies 50% or more of the total number of molecules. The second component includes the fluoroaluminosilicate glass powder (B) and the compound (D) containing a sulfur atom in one molecule, including a carboxylic group and an amino group and not including a polymerizable group. With the aforementioned configuration, the dental glass ionomer cement composition can be easily used only by mixing the two components. Thus, since the dental glass ionomer cement composition can be handled easily in a dental treatment, it is preferable.

Furthermore, the dental glass ionomer cement composition according to the present invention can further include a (meth)acrylate compound (E) and an room temperature polymerization type polymerization initiator (F). With this configuration, since visco-tenacity can be given to a cement body after curing, it is preferable.

Utility of the Invention

A dental glass ionomer cement composition according to the present invention includes a copolymer (A), a fluoroaluminosilicate glass powder (B), and water (C). The copolymer (A) includes a polymer or copolymer of α-β unsaturated carboxylic acid, or includes a copolymer of α-β unsaturated carboxylic acid and one or more kinds selected from a group of acrylamide, acrylonitrile, methacrylic acid ester, acrylates, vinyl chloride, allyl chloride and vinyl acetate. In the copolymer (A), the number of molecules of α-β unsaturated carboxylic acid occupies 50% or more of the total number of molecules. The dental glass ionomer cement composition is blended with a compound (D) which contains a sulfur atom in one molecule, includes a carboxylic group and an amino group, and does not include a polymerizable group. With this configuration, a functional group containing the sulfur atom in the compound (D) indicates compatibility with metal. Further, the carboxylic group and amino group in the compound (D) interact with the copolymer (A) by hydrogen bond, where the copolymer (A) mainly includes the polymer or copolymer of α-β unsaturated carboxylic acid as a matrix component of glass ionomer cement, or includes α-β unsaturated carboxylic acid. In addition, the carboxylic group and amino group in the compound (D) interact with a metallic element existing in the fluoroaluminosilicate glass powder (B). Therefore, high adhesion strength can be acquired. Furthermore, since the compound (D) does not include a polymerization group in its structure, decreasing of fitting strength caused by an easiness of polymerization does not occur.

Further, the compound (D) containing a sulfur atom in one molecule, including a carboxylic group and an amino group and not including a polymerizable group can have a structure in which the sulfur atom is not adjacent to an oxygen atom in the molecule. Further, the compound (D) containing a sulfur atom in one molecule, including a carboxylic group and an amino group and not including a polymerizable group can have a content of 0.01 to 10% by weight in the composition. Furthermore, the compound (D) containing a sulfur atom in one molecule, including a carboxylic group and an amino group and not including a polymerizable group has a structure in which the sulfur atom can have, in the molecule, a thiol (—SH) structure, a sulfide (—S—) structure or a disulfide (—S—S—) structure. With these configurations, the functional group containing the sulfur atom in the compound (D) indicates stronger compatibility to metal, so that it is preferable.

Further, the dental glass ionomer cement composition according to the present invention can be configured with a first component and a second component. The first component includes the copolymer (A) and water (C). The copolymer (A) includes a polymer or copolymer of α-β unsaturated carboxylic acid, or includes a copolymer of α-β unsaturated carboxylic acid and one or more kinds selected from a group of acrylamide, acrylonitrile, methacrylic acid ester, acrylates, vinyl chloride, allyl chloride and vinyl acetate. In the copolymer (A), the number of molecules of α-β unsaturated carboxylic acid occupies 50% or more of the total number of molecules. The second component includes the fluoroaluminosilicate glass powder (B) and the compound (D) containing a sulfur atom in one molecule, including a carboxylic group and an amino group and not including a polymerizable group. With the aforementioned configuration, the dental glass ionomer cement composition can be easily used only by mixing the two components. Thus, since the dental glass ionomer cement composition can be handled easily in a dental treatment, it is preferable.

Furthermore, the dental glass ionomer cement composition according to the present invention can further include a (meth)acrylate compound (E) and an room temperature polymerization type polymerization initiator (F). With this configuration, since visco-tenacity can be given to a cement body after curing, it is preferable.

DETAILED DESCRIPTION OF PREFERRED EMBODIMENT

The preferred embodiment of the present invention will be described below in detail.

The copolymer (A) includes a polymer or copolymer of α-β unsaturated carboxylic acid, or includes a copolymer of α-β unsaturated carboxylic acid and one or more kinds selected from a group of acrylamide, acrylonitrile, methacrylic acid ester, acrylates, vinyl chloride, allyl chloride and vinyl acetate. In the copolymer (A), the number of molecules of α-β unsaturated carboxylic acid occupies 50% or more of the total number of molecules. The α-β unsaturated carboxylic acid is α-β unsaturated monocarboxylic acid or α-β unsaturated dicarboxylic acid. The α-β unsaturated monocarboxylic acid is, for example, acrylic acid, methacrylic acid, 2-chloroacrylic acid or the like. The α-β unsaturated dicarboxylic acid is, for example, aconitic acid, mesaconic acid, maleic acid, itaconic acid, fumaric acid, glutamic acid, citraconic acid or the like. A homopolymer or a copolymer of acrylic acid or itaconic acid is the most preferable.

When the copolymer acquired by copolymerizing α-β unsaturated carboxylic acid and one or more kinds selected from a group of acrylamide, acrylonitrile, methacrylic acid ester, acrylates, vinyl chloride, allyl chloride and vinyl acetate is used, it is necessary to copolymerize those, so that the number of molecules of α-β unsaturated carboxylic acid occupies 50% or more of the total number of molecules in order to generate a sufficient ionic reaction with the fluoroaluminosilicate glass powder (B) described below.

The preferable weight average molecular weight of the copolymer (A) mainly including the polymer or copolymer of all unsaturated carboxylic acid or α-β unsaturated carboxylic acid is within a range from 4,000 to 40,000. A reason of this is that the copolymer (A) mainly including the polymer or copolymer of α-β unsaturated carboxylic acid or α-β unsaturated carboxylic acid is a component to be cured by reacting with the fluoroaluminosilicate glass powder (B) described below. In addition, if the weight average molecular weight of the copolymer (A) mainly including the polymer or the copolymer of α-β unsaturated carboxylic acid or α-β unsaturated carboxylic acid is less than 4,000, a problem is generated in the strength or durability of a cured material, and the adhesion strength to a tooth may decrease. Furthermore, if the weight average molecular weight exceeds 40,000, it is extremely difficult to knead the materials because consistency at kneading is too hard, so that it is not preferable.

The blending amount of the copolymer (A) mainly including the polymer or copolymer of α-β unsaturated carboxylic acid or α-β unsaturated carboxylic acid is desirably within a range from 3 to 25% by weight in the composition. If the blending amount is less than 3% by weight, the strength of a cured body tends to be low because an acid-base reaction with the fluoroaluminosilicate glass powder is insufficient. If the blending amount exceeds 25% by weight, kneading with the fluoroaluminosilicate glass powder and water comes to be difficult, so that it is not preferable.

As the fluoroaluminosilicate glass powder (B), a material conventionally used in dental cement can be used, and an aluminosilicate glass powder including $Al^{3+}$, $Si^{4+}$, $F^-$ and $O^{2-}$ as main components and further including $Sr^{2+}$ and/or $Ca^{2+}$ is preferably used. More specifically, as for the ratios of the main components, it is desirable that the fluoroaluminosilicate glass powder (B) includes, with respect to the total weight of glass, 10 to 21% by weight of $Al^{3+}$, 9 to 21% by weight of $Si^{4+}$, 1 to 20% by weight of F, and 10 to 34% by weight of the total of $Sr^{2+}$ and $Ca^{2+}$. The ratio of the fluoroaluminosilicate glass powder (B) in the composition is desirably 25 to 85% by weight. If the ratio is less than 25% by weight, the strength of the cured body is low. If the ratio exceeds 85% by weight, kneading with the copolymer (A) and water comes to be difficult, so that it is not preferable.

Water (C) is an indispensable component in the present invention. A reason of this is that a neutralization reaction of the fluoroaluminosilicate glass powder (B) with the copolymer (A) mainly including the polymer or copolymer of α-β unsaturated carboxylic acid or α-β unsaturated carboxylic acid is advanced under the existence of water. Further, in the dental glass ionomer cement composition according to the present invention, the neutralization reaction of the fluoroaluminosilicate glass powder (B) with the copolymer (A) mainly including the polymer or copolymer of α-β unsaturated carboxylic acid or α-β unsaturated carboxylic acid is advanced under the existence of the water (C), so that the dental glass ionomer cement composition adheres to a surface of a tooth. The blending amount of water to the composition is preferably 10 to 60% by weight.

The compound (D) containing a sulfur atom in one molecule, including a carboxylic group and an amino group and not including a polymerizable group is necessary to acquire strong adhesion strength because the carboxylic group and the amino group in the compound (D) interact with the copolymer (A) by hydrogen bond, where the copolymer (A) mainly includes the polymer or copolymer of α-β unsaturated carboxylic acid as a matrix component of glass ionomer cement, or includes α-β unsaturated carboxylic acid. In addition, the compound (D) is necessary to acquire strong adhesion strength because the compound (D) interacts with metal elements existing in the fluoroaluminosilicate glass powder (B). The compound containing a sulfur atom in one molecule, including a carboxylic group and an amino group and not including a polymerizable group could be, for example, D-cysteine hydrochloride-hydrate, DL-cysteine hydrochloride-hydrate, DL-homocysteine, L-cysteine, L-cysteine hydrochloride-hydrate, L-β, β-dimethylcysteine, N-acetyl-L-cysteine, DL-cysteine, D(-)-penicillamine, L-methionine, L-(-)-cysteine, thiomalic acid, or glutathione (reduction type). These can be used by mixing two or more kinds. Among those, L-cysteine is the most preferable in light of adhesiveness and biocompatibility.

Further, the compound (D) containing a sulfur atom in one molecule, including a carboxylic group and an amino group and not including a polymerizable group is a compound having a structure in which a sulfur atom is not adjacent to an oxygen atom in the molecule. With this structure, a functional group containing a sulfur atom in the compound (D) indicates higher compatibility with metal, so that it is preferable.

Further, the compound contains 0.01 to 10% by weight of the compound (D) containing a sulfur atom in one molecule, including a carboxylic group and an amino group and not including a polymerizable group. With this configuration, the sulfur atom in the compound (D) indicates higher compatibility with metal, so that it is preferable. If the content is less than 0.01% by weight, sufficient adhesive effect to metal cannot be expected. If the content exceeds 10% by weight, storage stability decreases, so that it is not preferable.

Furthermore, the compound (D) containing a sulfur atom in one molecule, including a carboxylic group and an amino group and not including a polymerizable group has a structure in which the sulfur atom has, in the molecule, a thiol (—SH) structure, a sulfide (—S—) structure or a disulfide (—S—S—) structure. With this structure, the sulfur atom in the compound (D) indicates stronger compatibility to metal, so that it is preferable. Particularly, when the compound (D) has the thiol (—SH) structure, it is more preferable.

In addition, it is preferable that the dental glass ionomer cement composition according to the present invention is configured with a first component and a second component. The first component includes the copolymer (A) and water (C). The copolymer (A) includes a polymer or copolymer of α-β unsaturated carboxylic acid, or includes a copolymer of α-β unsaturated carboxylic acid and one or more kinds selected from a group of acrylamide, acrylonitrile, methacrylic acid ester, acrylates, vinyl chloride, allyl chloride and vinyl acetate. In the copolymer (A), the number of molecules of α-β unsaturated carboxylic acid occupies 50% or more of the total number of molecules. The second component includes the fluoroaluminosilicate glass powder (B) and the compound (D) containing a sulfur atom in one molecule, including a carboxylic group and an amino group and not including a polymerizable group. With the aforementioned configuration, the dental glass ionomer cement composition can be easily used only by mixing the two components. Thus, since the dental glass ionomer cement composition can be handled easily in a dental treatment, it is preferable.

The dental glass ionomer cement composition of the present invention further includes a (meth)acrylate compound (E) and an room temperature polymerization type polymerization initiator (F). With this configuration, visco-tenacity can be given to a cement body after curing, so that it is preferable. The (meth)acrylate compound (E) could be methyl(meth)acrylate, ethyl(meth)acrylate, isopropyl(meth) acrylate, n-butyl(meth)acrylate, isobutyl(meth)acrylate, hydroxypropyl(meth)acrylate, tetrahydrofurfryl(meth)acrylate, glycidyl(meth)acrylate, 2-hydroxyethyl(meth)acrylate, 2-hydroxypropyl(meth)acrylate, 3-hydroxypropyl(meth) acrylate, 2-methoxyethyl(meth)acrylate, 2-ethoxyethyl (meth)acrylate, 2-ethylhexyl(meth)acrylate, benzyl(meth) acrylate, 2-hydroxy-1,3-di(meth)acryloxy propane, ethylene glycol di(meth)acrylate, diethylene glycol di(meth)acrylate, triethylene glycol di(meth)acrylate, butylene glycol di(meth) acrylate, neopentyl glycol di(meth)acrylate, 1,3-butanediol di(meth)acrylate, 1,4-butanediol di(meth)acrylate, 1,6-hexanediol di(meth)acrylate, trim ethylolpropane tri(meth)acrylate, trimethylolethane tri(meth)acrylate, pentaerythritol tri (meth)acrylate, trimethylolmethane tri(meth)acrylate, pentaerythritol tetra(meth)acrylate, polybutylene glycol di(meth)acrylate, or bisphenol A glycidyl(meth)acrylate. A monomer, an oligomer, and a prepolymer of these compounds can be properly used. Further, as for (meth)acrylate having an urethane bond, di-2-(meth)acryloxyethyl-2,2,4-trimethyl-hexamethylene dicarbamate, 1,3,5-tris[1,3-bis{(meth)acryloyloxy}-2-propoxycarbonylaminohexane]-1,3,5-(1H,3H, 5H)triazine-2,4,6-trione, and 2,2-bis-4-(3-(meth) acryloyloxy-2-hydroxypropyl)-phenylpropane, can be used. In addition, the (meth)acrylate having urethane bond could be a (meth)acrylate of an urethane oligomer including 2,2'-di(4-hydroxycyclohexyl) propane, 2-oxypanone, hexamethylene diisocyanate, and 2-hydroxyethyl(meth)acrylate, and a (meth)acrylate of an urethane oligomer including 1,3-butanediol, hexamethylene diisocyanate, and 2-hydroxyethyl(meth) acrylate. These (meth)acrylates and acrylates can be used independently or by mixing two or more kinds. The content of the (meth)acrylate compound (E) is preferably 5 to 30% by weight in the composition. If the content is less than 5% by weight, the improvement of the visco-tenacity of the composition cannot be expected. If the content exceeds 30% by weight, the (meth)acrylate compound (E) is not compatible with the copolymer (A) mainly including the polymer or copolymer of α-β unsaturated carboxylic acid or α-β unsaturated carboxylic acid. Thus, the strength of the cured body decreases, so that it is not preferable. In addition, it is preferable to increase polymerizability of the (meth)acrylate compound (E) that the (meth)acrylate compound (E) does not contain a sulfur atom and an acid group.

As the room temperature polymerization type polymerization initiator (F), a chemical polymerization catalysis such as an organic aromatic compound containing at least one —$SO_2$— group, i.e., aromatic sulfinic acid, its alkali salt, and an aromatic sulfonyl compound, can be used. More specifically, sodium p-toluenesulfinate, lithium p-toluenesulfinate, benzenesulfinic acid, sodium benzenesulfinate, p-toluenesulfonyl chloride, p-toluenesulfonyl fluoride, O-toluenesulfonyl isocyanate, sodium p-acetamidobenzenesulfinate and the like can be used. More preferably, sodium p-toluenesulfinate, sodium benzenesulfinate and the like can be used. In addition, there is no problem if these organic aromatic compounds containing at least one —$SO_2$— group can be a hydrate salt. These can be used independently or by mixing two or more kinds. Further, when the (meth)acrylate compound (E) at a side edge part of a metallic prosthesis is desired to be polymerized at first, a photopolymerization initiator such as camphoquinone (CQ) or 2,4,6-trimethylbenzoyl-diphenylphosphine oxide (TPO) can be further used, in addition to the room temperature polymerization type polymerization initiator (F).

As for the room temperature polymerization type polymerization initiator (F), the blending ratio is desirably 0.1 to 20% by weight with respect to the total amount of the (meth) acrylate compound. If the blending ratio is less than 0.1% by weight, polymerization of the (meth)acrylate compound (E) comes to be insufficient. If the blending ratio exceeds 20% by weight, the (meth)acrylate compound (E) is polymerized too fast, so that an operational surplus time comes to be short. Thus, it is not preferable in practical use. In addition, as a regulating agent for regulating a polymerization degree or a polymerization rate, a small amount of a polymerization inhibitor such as 6-tert-butyl-2,4-xylenol (IA) can be added.

In the dental glass ionomer cement composition according to the present invention, a thickener, a pigment and the like, which are conventionally used, can be blended properly as necessary.

EXAMPLES

As the fluoroaluminosilicate glass powders (B), glass powders I, II and III were produced respectively by fully mixing raw materials at the ratios illustrated in Table 1, holding each mixture for 5 hours at a melting temperature, cooling the mixture, pulverizing the melted mixture for 10 hours using a ball mill, and sieving the pulverized mixture with 200 meshes (ASTM). Further, these glass powders I, II and III were used at the ratios illustrated in Tables 2 and 3.

TABLE 1

| Materials | Fluoroaluminosilicate glass powders (B) | | |
|---|---|---|---|
| | I | II | III |
| Aluminum oxide (g) | 21 | 23 | 22 |
| Anhydrous silicic acid (g) | 44 | 41 | 43 |
| Calcium fluoride (g) | 12 | 10 | 12 |
| Calcium phosphate (g) | 14 | 13 | 15 |
| Strontium carbonate (g) | 9 | 13 | 8 |
| Melting temperature (° C.) | 1200 | 1100 | 1200 |

In the test illustrated in Table 2, the adhesion strengths to the metal of the dental glass ionomer cement including the liquid component (the first component) and the powder component (the second component) were compared between the examples including "the compound (D)" and the comparative examples not including "the compound (D)." In the test illustrated in Table 3, the adhesion strengths to the metal of the dental glass ionomer cement compositions including the first component and the second component which were both the pastes were compared between the examples including "the compound (D)" and the comparative examples not including "the compound (D)." In Tables 2 and 3, "the compound (D)" is containing a sulfur atom in one molecule, including a carboxylic group and an amino group and not including a polymerizable group.

The adhesion strength to the metal was evaluated referring to ISO/114405:2003 5.2.4. Namely, after a gold-silver-palladium alloy for dental casting (CASTWELL M.C. 〈12% GOLD〉, produced by GC Corporation) was casted, the casted alloy was wrapped and buried in a dental universal acrylic resin (UNIFAST II, produced by GC Corporation). Then, an adherend face was smoothed with a waterproof polishing paper of #120 and subjected to a sand blast treatment, and an adhesion area was determined by sticking a plastic tape (having a thickness of 0.1 mm) having an opening hole of 3 mm diameter. In the test illustrated in Table 2, the dental glass ionomer cement composition was produced by mixing and kneading 1 g of the liquid component (first component) and 2 g of the powder component (second component). In the test illustrated in Table 3, the dental glass ionomer cement composition was produced by mixing and kneading 1 g of the paste-like first component and 1 g of the paste-like second component. A test body was produced by coating the glass ionomer cement composition to a stainless rod having a diameter of 10 mm, pressing the stainless rod to the adherend face, and taking it into an incubator at humidity of 100% and 37° C. after 10 minutes from the beginning of kneading. After 1 hour from the beginning of kneading, the test body was soaked in distilled water at 37° C. for 23 hours. Then, the test body was subjected to a tensile test at a crosshead speed of 1 mm/min. Five tested bodies were produced for each example and comparative example and subjected to the tensile test. Average values of these results were illustrated in Tables 2 and 3.

In the test illustrated in Table 2, the adhesion strengths to the metal adhered body of comparative examples 1 to 3 were 3.6 to 4.3 MPa, where the comparative examples 1 to 3 did not include "the compound (D) containing a sulfur atom in one molecule, including a carboxylic group and an amino group and not including a polymerizable group." By contrast, the adhesion strengths of examples 1 to 5 including the compound (D) were 6.5 to 12.0 MPa. Therefore, it could be confirmed that the adhesion strengths were greatly improved.

TABLE 2

| | | | Example 1 | Example 2 | Example 3 | Example 4 | Example 5 |
|---|---|---|---|---|---|---|---|
| First Component (Liquid Component) | Copolymer (A) mainly including a polymer or a copolymer of a-b unsaturated carboxylic acid or a-b unsaturated carboxylic acid | polyacrylic acid | 45 | | 24.9 | 24.5 | |
| | | Copolymer of acrylic acid and Itaconic acid | | 45 | | | 19.9 |
| | Water (C) | Water | 55 | 55 | 33 | 33 | 38 |
| | (Meth)acrylate compound (E) | HEMA | | | 32 | 32 | 30 |
| | | TEGDMA | | | 5 | 5 | 6 |
| | | UDMA | | | 5 | 5 | 6 |
| | Other additives (photopolymerization initiator, polymerization inhibitor) | CQ | | | | 0.2 | 0 |
| | | TPO | | | | 0.2 | 0 |
| | | IA | | | 0.1 | 0.1 | 0.1 |
| | | Total (g) | 100 | 100 | 100 | 100 | 100 |
| Second Component (Powder Component) | Fluoroaluminosilicate glass powders (B) | Glass powder I | 99 | | 99.3 | | |
| | | Glass powder II | | 98 | | 99 | |
| | | Glass powder III | | | | | 98 |
| | Compound (D) containing a sulfur atom in one molecule, including a carboxylic group and an amino group and not including a polymerizable group | L-cysteine | 1 | | 0.2 | 0.5 | |
| | | L-methionine | | 2 | | | 1 |
| | Room temperature polymerization initiator (F) | Sodium p-toluenesulfinate | | | | 0.5 | 0.5 |
| | | Sodium benzenesulfinate | | | | | 1 |
| | | Total (g) | 100 | 100 | 100 | 100 | 100 |
| Adhesion test | Adhesion strength to a metal (tensile adhesion) [MPa] | | 8.5 | 6.5 | 10.4 | 12 | 9.7 |

| | | | Comparative example 1 | Comparative example 2 | Comparative example 3 |
|---|---|---|---|---|---|
| First Component (Liquid Component) | Copolymer (A) mainly including a polymer or a copolymer of a-b unsaturated carboxylic acid or a-b unsaturated carboxylic acid | polyacrylic acid | 40 | 24.5 | |
| | | Copolymer of acrylic acid and Itaconic acid | | | 20.9 |
| | Water (C) | Water | 60 | 30 | 35 |
| | (Meth)acrylate compound (E) | HEMA | | 35 | 32 |
| | | TEGDMA | | 5 | 6 |
| | | UDMA | | 5 | 6 |
| | Other additives (photopolymerization initiator, polymerization inhibitor) | CQ | | 0.2 | |
| | | TPO | | 0.2 | |
| | | IA | | 0.1 | 0.1 |
| | | Total (g) | 100 | 100 | 100 |
| Second Component (Powder Component) | Fluoroaluminosilicate glass powders (B) | Glass powder I | 100 | | |
| | | Glass powder II | | 99 | |
| | | Glass powder III | | | 99.5 |
| | Compound (D) containing a sulfur atom in one molecule, including a carboxylic group and an amino | L-cysteine | | | |
| | | L-methionine | | | |

TABLE 2-continued

|  |  |  | | | |
|---|---|---|---|---|---|
|  | group and not including a polymerizable group |  | | | |
|  | Room temperature polymerization initiator (F) | Sodium p-toluenesulfinate | | | 0.5 |
|  |  | Sodium benzenesulfinate | | 1 | |
|  |  | Total (g) | 100 | 100 | 100 |
| Adhesion test | Adhesion strength to a metal (tensile adhesion) [MPa] |  | 4.3 | 3.7 | 3.6 |

HEMA: 2-hydroxyethyl methacrylate
TEGDMA: Triethylene glycol dimethacrylate
UDMA: Di-2-methacryloxyethyl-2,2,4-trimethylhexamethylene dicarbamate
CQ: Camphoquinone
TPO: 2,4,6-trimethylbenzoyldiphenylphosphine oxide
IA: 6-tert-butyl-2,4-xylenol Furthermore, in the test illustrated in Table 3, the adhesion strengths to the metal adhered body of comparative examples 4 to 6 were 2.1 to 4.4 MPa, where the comparative examples 4 to 6 did not include "the compound (D) containing a sulfur atom in one molecule, including a carboxylic group and an amino group and not including a polymerizable group." By contrast, the adhesion strengths of examples 6 to 9 including the compound (D) were 7.2 to 11.2 MPa. Therefore, it could be confirmed that the adhesion strengths were greatly improved.

TABLE 3

|  |  |  | Example 6 | Example 7 | Example 8 | Example 9 | Comparative example 4 | Comparative example 5 | Comparative example 6 |
|---|---|---|---|---|---|---|---|---|---|
| First Component (paste) | Copolymer (A) mainly including a polymer or a copolymer of a-b unsaturated carboxylic acid or a-b unsaturated carboxylic acid | Polyacrylic acid | 35 |  | 35 |  | 34 |  |  |
|  |  | Copolymer of acrylic acid and Itaconic acid |  | 20 |  | 25 |  | 20 | 26 |
|  | Water (C) | Water | 35 | 40 | 35 | 50 | 38 | 40 | 40 |
|  | Room temperature polymerization initiator (F) | Sodium p-toluenesulfinate | 4 |  | 3 |  | 4 |  |  |
|  |  | Sodium benzenesulfinate |  | 2 |  | 3 |  | 2 | 3 |
|  | Filler | SiO$_2$ powder | 23 | 31 | 21 | 16 | 21 | 31 | 26 |
|  |  | AEROSIL | 3 | 7 | 6 | 6 | 3 | 7 | 5 |
|  |  | Total (g) | 100 | 100 | 100 | 100 | 100 | 100 | 100 |
| Second Component (paste) | Fluoroaluminosilicate glass powders (B) | Glass powder I | 69.8 |  |  |  | 69.9 |  |  |
|  |  | Glass powder II |  | 53.9 |  |  |  | 54.9 |  |
|  |  | Glass powder III |  |  | 63.5 | 54.0 |  |  | 64.5 |
|  | Compound (D) containing a sulfur atom in one molecule, including a carboxylic group and an amino group and not including a polymerizable group | L-cysteine | 0.1 | 1 |  |  |  |  |  |
|  |  | L-methionine |  |  | 1 |  |  |  |  |
|  |  | L-(-)-cysteine |  |  |  | 0.5 |  |  |  |
|  | (Meth)acrylate compound (E) | HEMA | 15 | 25 | 21 | 25 | 15 | 25 | 21 |
|  |  | TEGDMA | 5 | 5 | 3 | 5 | 5 | 5 | 3 |
|  |  | UDMA | 5 | 5 | 3 | 5 | 5 | 5 | 3 |
|  | Filler | AEROSIL | 5 | 10 | 8 | 10 | 5 | 10 | 8 |
|  | Other additives (photopolymerization initiator, polymerization inhibitor) | CQ |  |  | 0.2 | 0.2 |  |  | 0.2 |
|  |  | TPO |  |  | 0.2 | 0.2 |  |  | 0.2 |
|  |  | IA | 0.1 | 0.1 | 0.1 | 0.1 | 0.1 | 0.1 | 0.1 |
|  |  | Total (g) | 100 | 100 | 100 | 100 | 100 | 100 | 100 |
| Adhesion test | Adhesion strength to metal (tensile adhesion) [MPa] |  | 10.5 | 11.2 | 7.2 | 8.0 | 3.5 | 2.1 | 4.4 |

HEMA: 2-hydroxyethyl methacrylate
TEGDMA: Triethylene glycol dimethacrylate
UDMA: Di-2-methacryloxyethyl-2,2,4-trimethylhexamethylene dicarbamate
CQ: Camphoquinone
TPO: 2,4,6-trimethylbenzoyldiphenylphosphine oxide
IA: 6-tert-butyl-2,4-xylenol

What is claimed is:

1. A dental glass ionomer cement composition, consisting essentially of:
(A) a copolymer comprising
   (a1) a polymer or a copolymer of α-β unsaturated carboxylic acid, or
   (a2) a copolymer of α-β unsaturated carboxylic acid and at least one selected from the group consisting of acrylamide, acrylonitrile, methacrylic acid ester, acrylates, vinyl chloride, allyl chloride and vinyl acetate,
   wherein the number of molecules of α-β unsaturated carboxylic acid occupies 50% or more of the total number of molecules;
(B) a fluoroaluminosilicate glass powder;
(C) water; and
(D) a compound comprising a sulfur atom, a carboxylic group, and an amino group, wherein the compound (D) does not comprise a polymerizable group.

2. The composition of claim 1, wherein the compound (D) is a compound having a structure in which the sulfur atom is not adjacent to an oxygen atom in the molecule.

3. The composition of claim 1, wherein the dental glass ionomer cement composition contains 0.01 to 10% by weight of the compound (D).

4. The composition of claim 1, wherein the compound (D) is a compound having at least one selected from the group consisting of a thiol (—SH) structure, a sulfide (—S—) structure, and a disulfide (—S—S—) structure.

5. The composition of claim 1, consisting essentially of:
a first component comprising the copolymer (A) and water (C); and
a second component comprising the fluoroaluminosilicate glass powder (B) and the compound (D).

6. The composition of claim 1, wherein the compound (D) is at least one selected from the group consisting of D-cysteine hydrochloride-hydrate, DL-cysteine hydrochloride-hydrate, DL-homocysteine, L-cysteine, L-cysteine hydrochloride-hydrate, L-β,β-dimethylcysteine, N-acetyl-L-cysteine, DL-cysteine, D(–)-penicillamine, L-methionine, L-(–)-cysteine, thiomalic acid, and glutathione.

7. The composition of claim 6, wherein the compound (D) comprises L-cysteine or L-methionine.

8. A dental glass ionomer cement composition, consisting of:
(A) a copolymer comprising
   (a1) a polymer or a copolymer of α-β unsaturated carboxylic acid, or
   (a2) a copolymer of α-β unsaturated carboxylic acid and at least one selected from the group consisting of acrylamide, acrylonitrile, methacrylic acid ester, acrylates, vinyl chloride, allyl chloride and vinyl acetate,
   wherein the number of molecules of α-β unsaturated carboxylic acid occupies 50% or more of the total number of molecules;
(B) a fluoroaluminosilicate glass powder;
(C) water;
(D) a compound comprising a sulfur atom, a carboxylic group, and an amino group, wherein the compound (D) does not comprise a polymerizable group; and optionally, (F) a room temperature polymerization initiator comprising an aromatic sulfinic acid or an alkali salt thereof and/or an aromatic sulfonyl compound.

* * * * *